United States Patent [19]
Engelhard

[11] Patent Number: 5,266,215
[45] Date of Patent: Nov. 30, 1993

[54] WATER PURIFICATION UNIT

[76] Inventor: Rolf Engelhard, 10 Ridgecrest Dr., Prescott, Ariz. 86301

[21] Appl. No.: 55,264

[22] Filed: Apr. 27, 1993

[51] Int. Cl.⁵ .......................... C02F 1/32; C02F 1/78
[52] U.S. Cl. .................... 210/748; 210/192; 210/205; 210/450; 210/451; 210/453; 210/760; 210/764; 250/436; 422/24; 422/186.3
[58] Field of Search ............ 210/748, 760, 764, 198.1, 210/205, 192, 450, 451, 453; 422/24, 186.3; 250/435, 436, 437, 438; 261/DIG. 42

[56] References Cited

U.S. PATENT DOCUMENTS

| | | | |
|---|---|---|---|
| 3,696,932 | 10/1972 | Rosenberg | 210/437 |
| 4,892,712 | 1/1990 | Robertson et al. | 210/763 |
| 5,106,501 | 4/1992 | Yang et al. | 210/437 |
| 5,178,758 | 1/1993 | Hwang | 210/748 |

Primary Examiner—Neil M. McCarthy
Attorney, Agent, or Firm—Cahill, Sutton & Thomas

[57] ABSTRACT

Water to be purified swirls about a source of ultraviolet radiation to kill any microorganisms contained therein and flows through a carbon filter cartridge mounted about the ultraviolet source to remove any chlorine and particulate matter. The outflow from the carbon filter is again subjected to ultraviolet radiation to kill any microorganisms entrained in the water emanating from the carbon filter. An ozone generator may be incorporated to entrain ozone with the inflowing water to enhance killing of any microorganisms present and to oxidize any undesirable compounds.

22 Claims, 3 Drawing Sheets

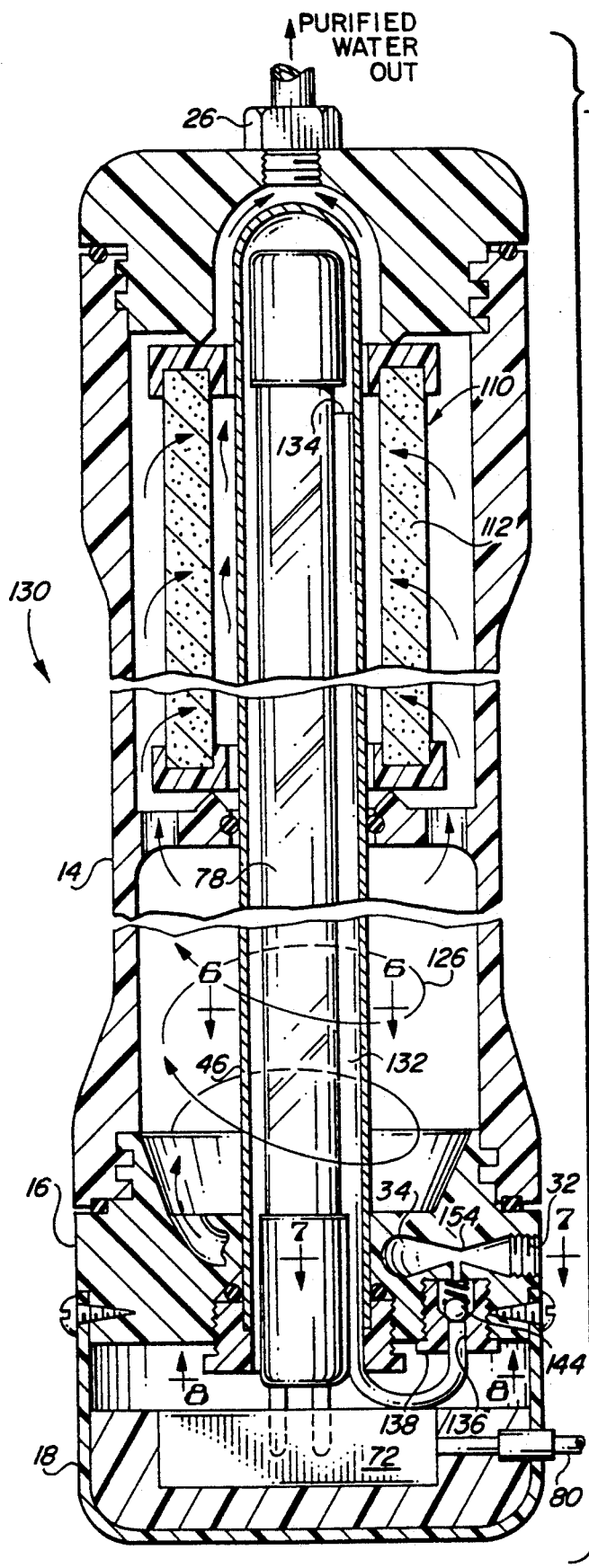
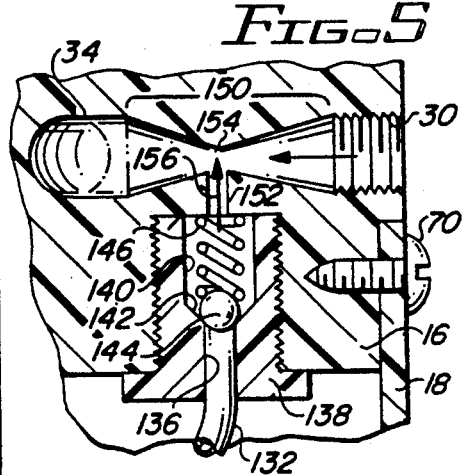
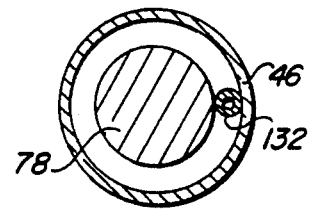
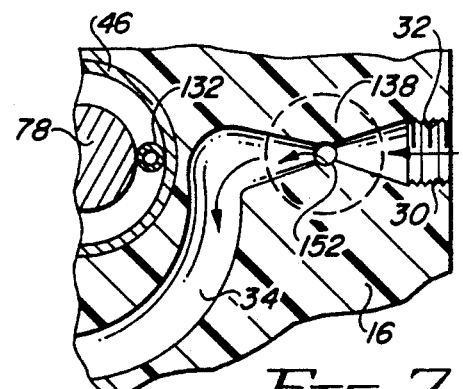
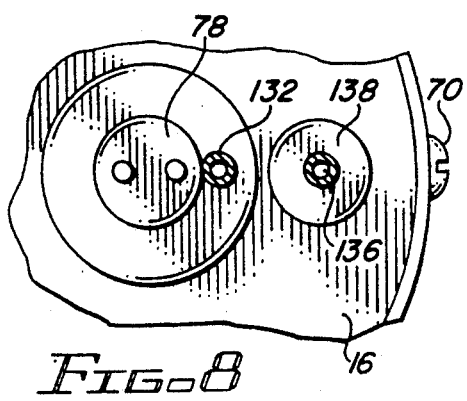

WATER PURIFICATION UNIT

BACKGROUND OF THE INVENTION

1. Field of the Invention

The present invention relates to water purification systems and, more particularly, to apparatus for destroying living microorganisms flowing into and out of a filter for removing any particulate matter that may be present.

2. Description of Related Art

For decades various water filtering and purifying devices have been used by consumers. Some of these devices perform primarily only a filtering system to remove particulate matter. Some of these systems incorporate activated charcoal as a filtering medium to remove chlorine from the water obtained from municipal water sources. Some devices incorporate a source of ultraviolet light to help kill living microorganisms. To enhance such killing and to oxidize various compounds in the water, ozone may be injected into and mixed with the water.

While activated charcoal filters can be very effective in removing particulate matter and chlorine from water, they suffer a major drawback. The contaminants or sludge filtered from the water will collect upon the filter. The sludge, particularly when it contains organic matter, serves as a breeding ground for bacteria, viruses and other microorganisms. These microorganisms often are conveyed from the filter downstream and ultimately ingested by the consumer. This potential health hazard can be avoided to some extent by regular replacement of the filtering medium. Unfortunately, such replacement is often neglected by a consumer and the resulting health hazard may be life threatening. To avoid and eliminate such a health hazard, the use of consumer oriented water filtering devices having mechanical filters for removing particulate matter has been banned in various communities around the world.

SUMMARY OF THE INVENTION

Water to be purified flows within a canister in a swirling pattern about a source of ultraviolet radiation to subject any living microorganisms to the killing effect of ultraviolet radiation. The water flows through a cartridge filter to remove particulate matter and also chlorine if the filter contains activated charcoal. Outflow from the filter is again subjected to ultraviolet radiation to kill any microorganisms that grew in residue upon the filter and subsequently became entrained in the outflowing water. To enhance killing of any microorganisms, an ozone generator may be incorporated to provide ozone for entrainment with water inflowing to the canister.

It is therefore a primary object of the present invention to provide a water purification apparatus having an outflow free of living microorganisms and particulate matter.

Another object of the present invention is to provide a source of ultraviolet radiation for killing microorganisms flowing into and out of a filter of a water purification apparatus.

Still another object of the present invention is to provide apparatus for mounting a cartridge filter upon a source of ultraviolet radiation within a canister of a water purification apparatus.

Yet another object of the present invention is to provide a water purification apparatus having a readily replaceable cartridge filter and source of ultraviolet radiation for irradiating the water flowing into and out of the cartridge filter and the surface of the filter from which the water flows.

A further object of the present invention is to provide a water purification apparatus for generating and mixing ozone with inflowing water swirling about a source of ultraviolet radiation to provide a combined effect for killing microorganisms before and after passage of the water through a filter medium.

A yet further object of the present invention is to provide an ozone generator within a water purification apparatus incorporating a source of ultraviolet radiation and a cartridge filter.

A still further object of the present invention is to provide a method for purifying water.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 4 is a cross-sectional view of a variant water purification apparatus;

FIG. 5 is a detail view of apparatus for entraining ozone in the inflowing water;

FIG. 6 is a cross-sectional view taken along lines 6—6, as shown in FIG. 4;

FIG. 7 is a cross-sectional view taken along lines 7—7, as shown in FIG. 4;

FIG. 8 is a detail view taken along lines 8—8, as shown in FIG. 1;

DESCRIPTION OF THE PREFERRED EMBODIMENT

Figure 1:
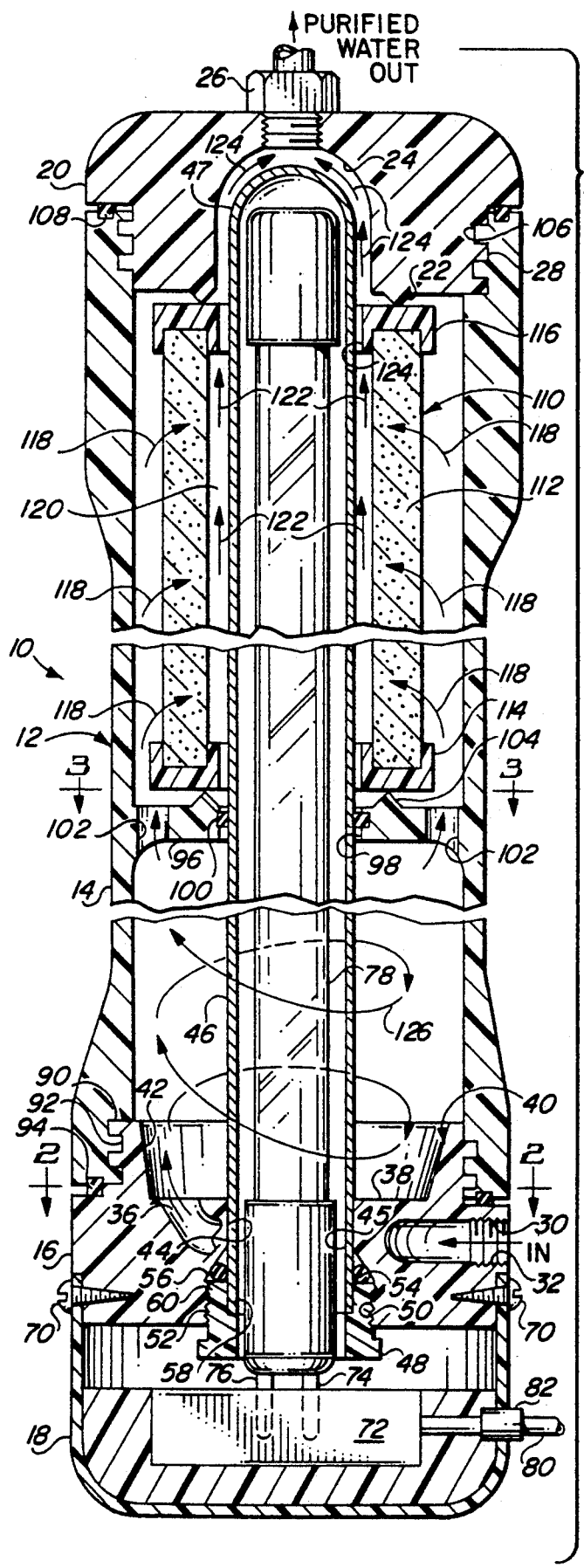
FIG. 1 is a cross-sectional view illustrating a water purification apparatus.

Referring to FIG. 1, there is illustrated a water purification water apparatus 10 in the general shape of a canister 12. The sleeve member includes a central sleeve member 14 for conveying water longitudinally therein during purification. The canister is detachably attached to a water inlet member 16. A base 18 attached to the water inlet member supports canister 12. A top member 20 is detachably attached to the upper end of sleeve member 14 for closing the upper end of the sleeve member and for providing an outlet for the water purified within water purification apparatus 10.

Figure 2:
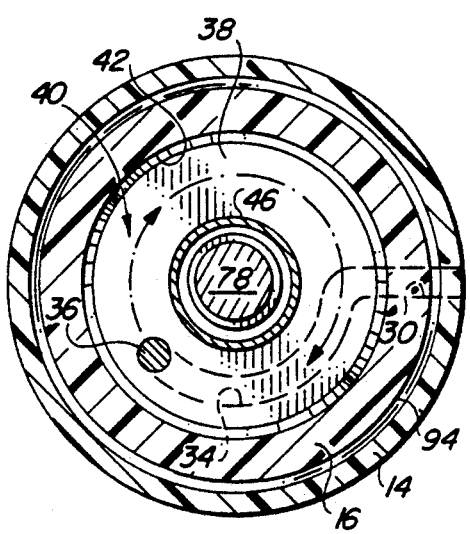
FIG. 2 is a cross-sectional view taken along lines 2—2, as shown in FIG. 1.
Figure 3:
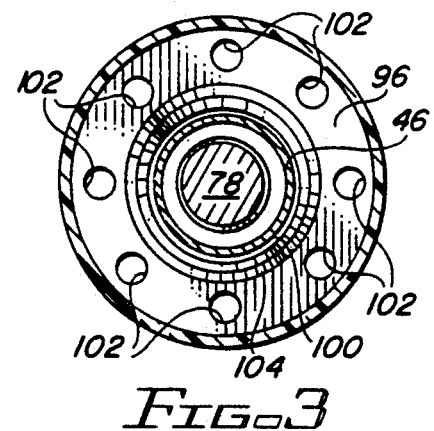
FIG. 3 is a cross-sectional view taken along lines 3—3, as shown in FIG. 1.

As shown in FIGS. 1 and 2, water inlet member 16 includes an inlet 30, which inlet may include internal threads 32 for threaded engagement with a nipple or conduit conveying water to the water inlet member. The inlet is in communication with a passageway 34 for conveying the inflowing water to outlet 36, which outlet is disposed in base 38 of depression 40 formed in water inlet member 16. The orientation of outlet 36, in combination with the adjacent section of passageway 34, directs the outflow against cone shaped wall 42 of depression 40 to induce a circular or swirling motion of the inflowing water. A passageway 44 extends through the center of water inlet member 16 for receiving and supporting the bottom open end 45 of a tube 46 having a closed top end 47. An apertured collar 48 is in threaded engagement with threads 50 disposed in radially expanded section 52 of passageway 44. An O-ring 54 encircles bottom end 45 of tube 46 adjacent shoulder 56 of passageway 44. Collar 48 may include a radially expanded depression 58 for receiving and supporting bottom end 45 of tube 46. Upon tightening of collar 48, tube 46 is moved axially within passageway 44 due to the force exerted upon it by depression 58. O-ring 54 will be compressed between shoulder 56 and the adjacent cylindrical surface of tube 46 by end 60 of the collar to form a water tight seal between the cylindrical surface of the tube and passageway 44.

Base 18, being cup shaped, as illustrated, may be secured to water inlet member 16 by fastening means, such as screws 70. A socket 72 is formed within the base to support and electrically engage prongs 74, 76 of ultraviolet (UV) light 78. This light emits ultraviolet radiation; necessarily, tube 46 must be transmissive to such radiation and it is therefore preferable that the tube be made of quartz or similar material. Socket 72 also includes an electrical circuit necessary to energize ultraviolet (UV) light 78. Electrical power for the circuit is provided by conductor 80 extending from base 18 through grommet 82 or the like. Conductor 80 is electrically connected to a source of electrical power (not shown) such as a source of 12vdc).

Sleeve member 14 includes internal threads 90 for threadedly engaging threads 92 at the upper end of water inlet member 16 and encircling depression 40. Upon threaded engagement between the sleeve member and the water inlet member, O-ring 94 disposed therebetween is compressed to provide a watertight engagement. A radial flange 96 disposed within sleeve member 14 includes a central aperture 98 for accommodating penetrable engagement of tube 46. An o-ring 100 disposed therebetween prevents water flow intermediate tube 46 and aperture 98 of flange 96. A plurality of passageways 102 are disposed in flange 96 to permit water flow therethrough into the upper end of sleeve member 14.

A filter cartridge 110 of any one of many types of commercially available filter cartridges is penetrably mounted upon tube 46; it may include activated carbon/charcoal to remove chlorine and other similar compounds. Such a cartridge includes a cylindrical filter element 112 having annular support members 114, 116 disposed at opposed ends. These support members are generally of rubber, neoprene, or the like. Radial flange 96 includes an annular ridge 104 for supporting cartridge filter 110 by contact with support member 114. The annular ridge, in compressive engagement with ridge 104, establishes a seal therebetween. Such seal precludes water flowing through passageways 102 from flowing intermediate flange 96 and the lower end of filter cartridge 110 into the annular interior of the filter cartridge. Accordingly, all water flowing from passageways 102 flows to the exterior of filter element 112, as depicted by arrows 118 and through the filter element. Top member 20 includes a similar annular ridge 22 for compressively engaging support member 116 to prevent flow of water between the top member and the upper end of filter cartridge 110. Thus, all water flowing through passageways 102 must flow through the filter cartridge from the outer surface to the inner surface.

Support members 114 and 116 are annular in configuration and may have internal diameters greater than the diameter of tube 46, as depicted. Water flowing through filter element 112, as depicted by arrows 118, flows into the annular space interior of the filter element and adjacent tube 46, which space is identified by numeral 120. The water flow through space 120 is upwardly, as depicted by arrows 122. Outflow from space 120 is through the annular channel defined between annular surface 124 of support member 116 and the cylindrical surface of tube 46.

Top member 20 includes a depression 24 for receiving the top end 47 of tube 46. The depression is sized sufficiently greater than the top end of the tube to permit flow of water adjacent the tube, as depicted by arrows 124. An outlet fixture 26 is secured to and extends from top member 20 to accommodate outflow of water from depression 24.

Top member 20 is detachably attached to the upper end of sleeve member 14 by threads 28 of the top member engaging threads 106 of the sleeve member. A water tight fit is assured by O-ring 108 compressed between the top member and the sleeve member upon threaded engagement therebetween.

In operation, water to be filtered enters through inlet 30 in water inlet member 16 and is discharged through outlet 36. The angle of discharge causes the water to flow in a circular path within sleeve 14 in a helical manner, as depicted by helical arrow 126. The circular water flow is enhanced in part by cone shaped wall 42 in the water inlet member. The water swirling about tube 46 is subjected to UV radiation from UV light 78. As is well known, any living microorganisms, whether bacteria, viruses, etc. will be killed upon UV irradiation. Moreover, certain compounds, if present in the water, may be oxidized to enhance purification of the water. The water swirling about tube 46 will enhance exposure of all of the living microorganisms to UV radiation and thereby a more complete killing of the microorganisms is enhanced. The swirling water will also perform a scrubbing action upon tube 46 to help maintain it clean and clear. The swirling water ultimately flows through passageways 102 to the outer surface of filter element 112. Flow of the water through the filter element will cause removal of particulate matter, including dead living microorganisms. The water discharged from the interior surface of filter element 112 flows adjacent tube 46, as depicted by arrows 122 to again subject the water to UV irradiation. Any living microorganisms entrained in the water flowing from the filter element will be killed through the resulting UV irradiation. Furthermore, the inner surface of the filter element from which the water is discharged will be irradiated by UV to kill any residual microorganisms that may attempt to grow there. The filtered and purified water flows into depression 24 and is discharged through outlet 26 to a point of use.

At greater or lesser intervals, depending upon the degree of contamination of the inflowing water, filter cartridge 110 should be replaced. Such replacement is readily effected by simply unscrewing top member 20 from sleeve member 14 and withdrawing the cartridge filter from about tube 46. A replacement filter is mounted upon the tube and the top member is screwed on to the sleeve member to lock the filter in place and provide a watertight seal between the sleeve member and the top member.

Referring jointly to FIGS. 4–8, there is shown a variant 130 of the water purification unit. For ease of reference and correlation between water purification unit 10 and 130, common elements will be identified with common reference numerals. Variant 130 is similar in structure, function and operation to water purification unit 10 but includes a further capability of generating ozone and entraining the generated ozone in the inflowing water to enhance killing of any microorganisms and to enhance oxidation of certain compounds.

It is well known that ultraviolet radiation in air will alter the molecular structure of oxygen ($O_2$), to produce ozone ($O_3$). Since ultraviolet light 78 is located in an air environment or air space within tube 46, some of the oxygen molecules in the air space between the light and the tube will be converted to ozone molecules. Furthermore, these ozone molecules will collect at closed top end 47 of tube 46. A conduit 132 is disposed within tube 46 adjacent UV light 78. Inlet 134 of the conduit is disposed proximate the top end of tube 46. The lower end of the conduit extends from within tube 46 into passageway 136 of a plug 138. The plug is in threaded engagement with water inlet member 16. A radially expanded section 140 of passageway 136 includes cone shaped annular bottom surface 142. A ball 144, located adjacent surface 142 in response to in a coil spring 146, serves in the manner of a check valve to permit flow from conduit 132 into expanded section 140 but not in reverse Inlet 30 for the water to be purified, is directed through a venturi section 150. A passageway 152 interconnects expanded section 140 with the diametrically restricted section 154 of venturi section 150. As is well known, and in accordance with the Bernoulli principle, the pressure at section 154 will be below ambient pressure. Accordingly, an inflow, as depicted by arrow 156 will occur. The inflow results in a reduced pressure in expanded section 140 below that present within conduit 132. Accordingly, ozone will flow from conduit 132 into the expanded section, through conduit 152 and into venturi section 150. Because of the difference in pressure on opposed sides of ball 144, the check valve will open. Reverse flow through the check valve is precluded by the sealing engagement of ball 144 with the outlet of conduit 132 under urging of spring 146. It may be noted that an 0-ring or other sealing member may be incorporated intermediate plug 138 and water inlet member 16 to ensure that water will not leak into base 18.

In operation, water flow from inlet 30 through venturi section 150 will draw a flow of air, and any ozone present, into inlet 134 of conduit 132 for discharge past ball 144 through expanded section 140 and into section 154. The resulting entrainment of air and ozone will be swirled about tube 46, as depicted by arrow 126. The presence of ozone in the water, will, by itself, result in killing of living microorganisms present and oxidation of certain compounds, if present. Thus, any living microorganisms present in the water within sleeve member 14 will be subjected to the killing effect of both UV radiation from light 78 and ozone. Filter element 112 of filter cartridge 110 will remove any particulate matter that may be present, including residue of any killed microorganisms. To the extent ozone flows into filter element 112, it will kill any living microorganisms on the surface of the filter into which the water flows. To the extent that any living organisms are entrained in the water outflowing from the interior surface of filter element 112, they are again irradiated with UV radiation from light 78 prior to discharge through outlet 26. To the extent any ozone may be present in the water flowing through and from the filter element, killing of the microorganisms will be enhanced.

Figure 9:
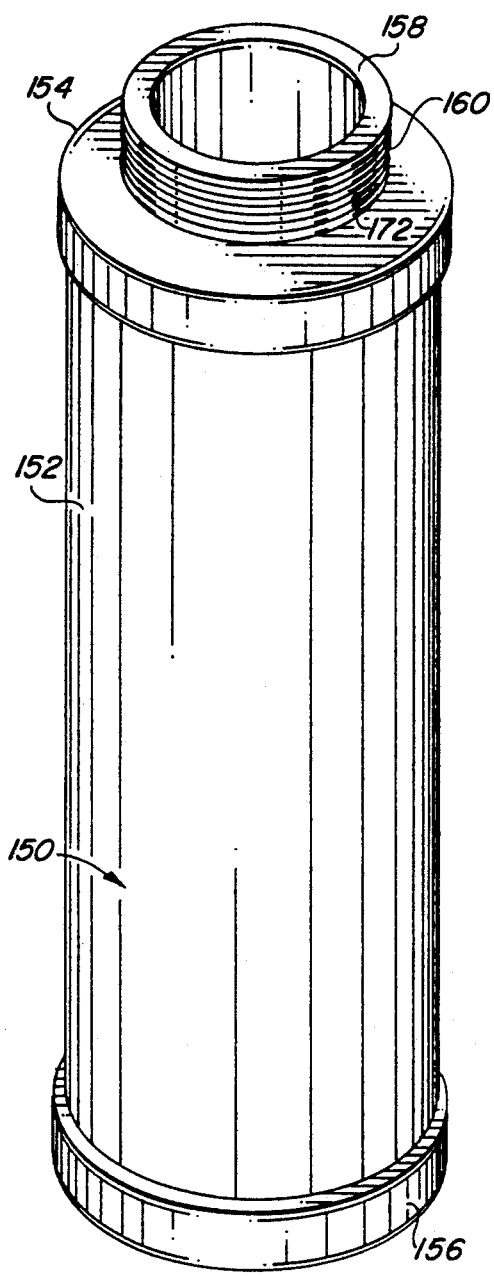
FIG. 9 illustrates a variant of the filter element.
Figure 10:
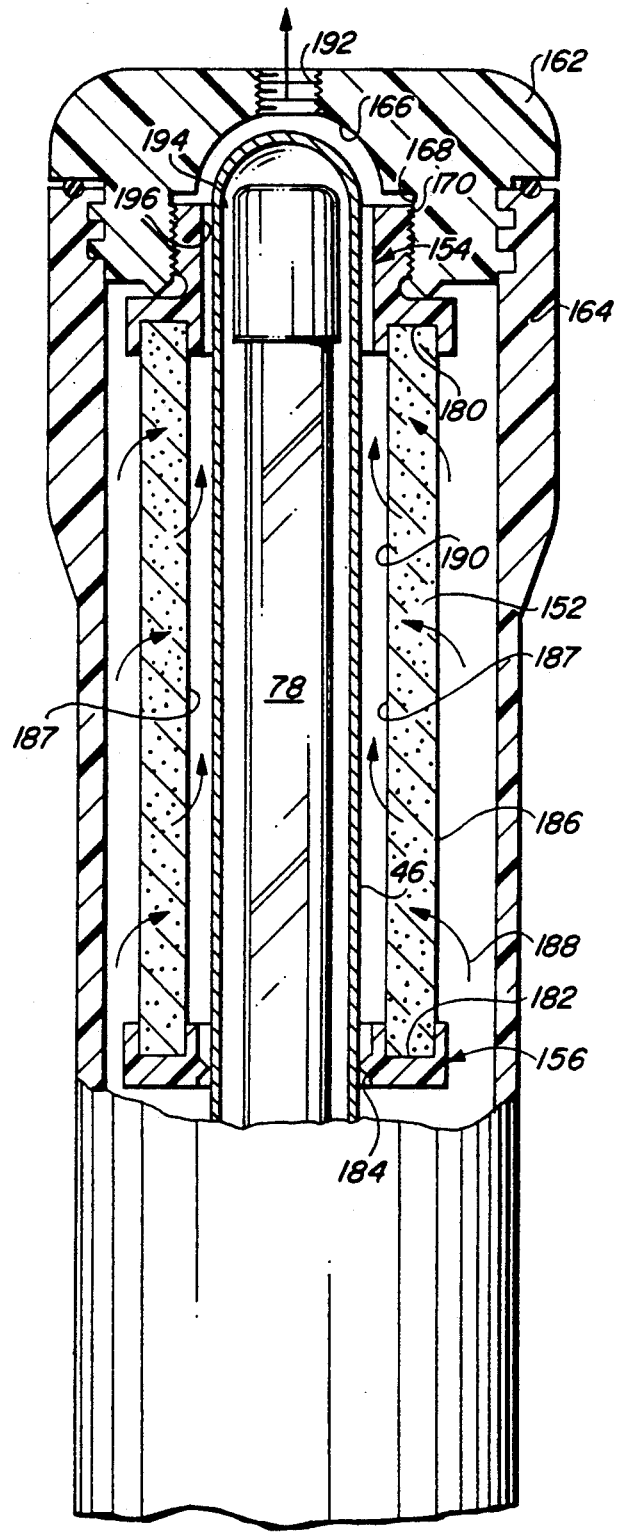
FIG. 10 is a partial cross sectional view of the variant filter element in place within the apparatus.

Referring jointly to FIGS. 9 and 10, there is illustrated a variant 150 of filter cartridge 110 (see FIGS. 1 and 4) which eliminates the need for flange 96 in sleeve member 14. The variant includes a cylindrical filter element 152 having an apertured cap 154 at one end and an annular retainer 156 at the other end. Cap 154 includes a hollow boss 158 extending upwardly therefrom and having external threads 160 formed thereon. Top member 162, is in threaded engagement with sleeve member 164, as described above with respect to apparatus 10 and variant 130. Proximate the lower end of depression 166 in the top member there is an annular ring 168 supporting threads 170. Threads 170 are configured to threadedly engage threads 172 encircling boss 160 to provide engagement with and support for variant 150.

Cap 154 includes a groove 180 for receiving and supporting cylindrical filter element 152. Annular retainer 156 includes a groove 182 for receiving and supporting the other end of cylindrical filter 152. In addition, annular retainer 156 includes a radially inwardly oriented ridge 184 for sealingly engaging the exterior cylindrical surface of tube 46 encasing UV light 78. Preferably, annular retainer 156 is of compressible plastic material to compressively retain the filter element and to better develop and maintain the seal about tube 46.

In operation, water flowing upwardly through sleeve member 160 from below annular retainer 156 will be forced past the annular retainer and proximate exterior surface 186 of filter element 152, as depicted by arrows 188. Thereafter the water flows interiorly through the filter element and proximate tube 46, as depicted by arrows 190. Water is discharged through outlet 192 via annular passageway 194 intermediate tube 46 and interior wall 196 and via depression 166. Ridge 184 of the annular retainer channels the water to the exterior surface of filter element 152 and precludes outflow of water which has not been filtered through filter element.

From the above description of variant 150, it will become evident that the variant eliminates the need for flange 96 to direct water flow to the exterior surface of filter element 152. Yet, the configuration of the variant ensures filtration of the water flow and exposure of the filtered water to irradiation by UV light 78. Moreover, interior surface 187 of filter element 152 will be irradiated to kill any bacteria, virus or microorganism that may be present at or proximate such surface.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. A water purification apparatus comprising in combination:
   (a) a sleeve member having first and second end portions;

(b) a source of UV radiation for killing microorganisms present in the water to be purified, said UV source being disposed within said sleeve member and having first and second end sections;

(c) an inlet member disposed in said first end portion of said sleeve member for introducing unfiltered water into a first space defined by said first end portion of said sleeve member and said first end section of said UV source to subject the unfiltered water to UV radiation for killing microorganisms and to produce irradiated unfiltered water;

(d) a filter element located in said second end portion of said sleeve member and disposed proximate said second end section of said UV source and having an inner surface juxtaposed with said second end section of said UV source to define a second space between said UV source and said inner surface of said filter element for irradiating filtered irradiated water flowing into and through said second space, said filter element including an outer surface;

(e) means for introducing the irradiated unfiltered water to said outer surface of said filter element;

(f) means for preventing direct flow of unfiltered irradiated water from said first space to said second space and for directing flow of irradiated unfiltered water from said first space through said filter element into said second space to filter the irradiated unfiltered water flowing through said filter element and to produce filtered irradiated water flowing into said second space; and (g) means for discharging form said apparatus the filtered twice irradiated water irradiated within and flowing through said second space.

2. The apparatus as set forth in claim 1 including means for swirling the unfiltered water about said UV source to enhance exposure of any water entrained microorganisms to UV irradiation.

3. The apparatus as set forth in claim 1 wherein said filter element comprises a cartridge filter.

4. The apparatus as set forth in claim 3 including means for supporting said cartridge filter upon said UV source.

5. The apparatus as set forth in claim 4 including means for locating said cartridge filter in an encircling relationship with said UV source.

6. The apparatus as set forth in claim 1 including means for channeling the unfiltered irradiated water from said first space to said outer surface and further means for channeling the filtered irradiated water from said second space to said discharging means.

7. The apparatus as set forth in claim 1 wherein said UV source comprises an elongated cylindrical lamp and including an UV transmissive tube for surrounding and for protecting said lamp.

8. The apparatus as set forth in claim 7 wherein said filter element comprises a cartridge filter and including means for penetrably mounting said cartridge filter upon said tube.

9. The apparatus as set forth in claim 8 including means for channeling the unfiltered irradiated water from said first space to said outer surface and further means for channeling filtered irradiated water from said second space to said discharging means.

10. The apparatus as set forth in claim 9 wherein said mounting means comprises said channeling means.

11. The apparatus as set forth in claim 9 including means for removably mounting said cartridge filter within said apparatus.

12. The apparatus as set forth in claim 7 including a base for supporting said lamp and means for detachably attaching said base with said sleeve member to accommodate replacement of said lamp.

13. The apparatus as set forth in claim 12 wherein said filter element comprises a cartridge filter and means for removably mounting said cartridge filter upon said lamp.

14. The apparatus as set forth in claim 1 including means for generating ozone within said apparatus and means for entraining the ozone with the unfiltered irradiated water within said first space to kill microorganisms.

15. The apparatus as set forth in claim 14 wherein said entraining means comprises a venturi for entraining the ozone with the water introduced through said inlet member.

16. The apparatus as set forth in claim 15 wherein said generating means comprises an air space adjacent said UV source and wherein said entraining means includes a conduit extending from the air space to said venturi.

17. The apparatus as set forth in claim 16 including means for limiting flow through said conduit in one direction.

18. A method for purifying water within an apparatus having a sleeve member housing a UV source and a filter element, said method comprising the steps of:

(a) introducing unfiltered water through an inlet into a first space defined by a first portion of the sleeve member and a first section of the UV source;

(b) irradiating the unfiltered water within the first space by subjecting the unfiltered water to UV radiation to kill microorganisms and to produce irradiated unfiltered water;

(c) introducing the irradiated unfiltered water to an outer surface of the filter element;

(d) filtering the irradiated unfiltered water through the filter element;

(e) irradiating the filtered irradiated water within a second space defined by an inner surface of the filter element located in a second portion of the sleeve member and a second section of the UV source, and (f) discharging the twice irradiated filtered water from the sleeve member.

19. The method as set forth in claim 18 including the steps of generating ozone within the apparatus and entraining the unfiltered water with the generated ozone.

20. The method as set forth in claim 18 wherein the UV source includes a tube having an elongated lamp for radiating the ultraviolet radiation and the filter element includes a cartridge filter for filtering the irradiated unfiltered water, and including the step of penetrably supporting the cartridge filter upon the tube.

21. The method as set forth in claim 18 including the step of entraining ozone with the unfiltered water.

22. The method as set forth in claim 21 including the step of generating within the apparatus the ozone to be entrained.

* * * * *